(12) United States Patent
Nelson

(10) Patent No.: US 8,926,642 B2
(45) Date of Patent: Jan. 6, 2015

(54) METHOD FOR EXTRACTING TUBULAR STRUCTURES

(71) Applicant: Nelson Medical Enterprises, LLC, North Olmsted, OH (US)

(72) Inventor: Dvora Y. Nelson, Westlake, OH (US)

(73) Assignee: Nelson Medical Enterprises, LLC, North Olmsted, OH (US)

( * ) Notice: Subject to any disclaimer, the term of this patent is extended or adjusted under 35 U.S.C. 154(b) by 0 days.

(21) Appl. No.: 13/865,332

(22) Filed: Apr. 18, 2013

(65) Prior Publication Data

US 2013/0204282 A1   Aug. 8, 2013

Related U.S. Application Data

(62) Division of application No. 12/953,267, filed on Nov. 23, 2010, now abandoned.

(60) Provisional application No. 61/313,899, filed on Mar. 15, 2010, provisional application No. 61/263,531, filed on Nov. 23, 2009.

(51) Int. Cl.
*A61B 17/32* (2006.01)
*A61B 17/00* (2006.01)
*A61B 17/3205* (2006.01)
*A61B 19/00* (2006.01)
*A61B 17/29* (2006.01)
*A61B 17/34* (2006.01)

(52) U.S. Cl.
CPC ... *A61B 17/320016* (2013.01); *A61B 17/00008* (2013.01); *A61B 17/32056* (2013.01); *A61B 19/5202* (2013.01); *A61B 2017/00349* (2013.01); *A61B 2017/2904* (2013.01); *A61B 2017/2924* (2013.01); *A61B 2017/2925* (2013.01); *A61B 2017/3484* (2013.01); *F17C 2201/0109* (2013.01); *F17C 2203/0607* (2013.01); *F17C 2203/0636* (2013.01); *F17C 2203/0643* (2013.01); *F17C 2203/0646* (2013.01); *F17C 2203/0648* (2013.01); *F17C 2205/0323* (2013.01); *F17C 2209/2172* (2013.01); *F17C 2209/225* (2013.01); *F17C 2221/032* (2013.01); *F17C 2223/0123* (2013.01); *F17C 2223/0153* (2013.01); *F17C 2260/01* (2013.01); *F17C 2265/01* (2013.01); *F17C 2270/0518* (2013.01)
USPC ............................................. 606/159

(58) Field of Classification Search
CPC .......... A61B 17/00008; A61B 17/221; A61M 1/0078
USPC ............................ 606/110, 113, 159
See application file for complete search history.

(56) References Cited

U.S. PATENT DOCUMENTS 3,508,553 A    4/1970  Kanbar et al.
5,171,233 A *  12/1992 Amplatz et al. .............. 604/540

(Continued)

OTHER PUBLICATIONS

European Patent Office, International Search Report and Written Opinion in PCT Application No. PCT/US2010/057895, May 24, 2011.

*Primary Examiner* — Ryan Severson
*Assistant Examiner* — Anh Dang
(74) *Attorney, Agent, or Firm* — Wood, Herron & Evans, L.L.P.

(57) ABSTRACT

A method for extracting a tubular structure from tissue using a device including a handle having an actuator, an elongate body with a first end coupled to and extending from the handle, and an operational head disposed at a second end of the elongate body. The operational head is longitudinally movable between a neutral position and an actuated position. The method includes inserting the elongate body into the tubular structure; placing the operational head into the actuated position; engaging the tubular structure with the operational head when in the actuated position; and pulling the tubular structure from the tissue by moving the operational head.

4 Claims, 6 Drawing Sheets

(56) References Cited

U.S. PATENT DOCUMENTS

| | | |
|---|---|---|
| 5,746,747 A | 5/1998 | McKeating |
| 5,758,665 A | 6/1998 | Suval |
| 5,843,104 A | 12/1998 | Samuels |
| RE36,043 E | 1/1999 | Knighton |
| 5,899,913 A | 5/1999 | Fogarty et al. |
| 6,036,713 A | 3/2000 | Kieturakis |
| 6,068,639 A | 5/2000 | Fogarty et al. |
| 6,527,787 B1 | 3/2003 | Fogarty et al. |
| 6,551,335 B1 * | 4/2003 | Bardeau et al. ............... 606/159 |
| 6,652,549 B1 | 11/2003 | Welten |
| 6,887,251 B1 | 5/2005 | Suval |
| 7,163,546 B2 | 1/2007 | Mirizzi et al. |
| 2003/0109874 A1 | 6/2003 | Dennis |
| 2004/0087967 A1 | 5/2004 | Schur et al. |
| 2004/0092990 A1 | 5/2004 | Opie et al. |
| 2008/0161841 A1 | 7/2008 | Clague et al. |
| 2011/0264124 A1 | 10/2011 | Boyle et al. |

* cited by examiner

METHOD FOR EXTRACTING TUBULAR STRUCTURES

CROSS-REFERENCE TO RELATED APPLICATIONS

This application is a divisional of U.S. application Ser. No. 12/953,267, filed Nov. 23, 2010 (pending) and claims benefit of U.S. Provisional Application Ser. No. 61/313,899, filed on Mar. 15, 2010 (expired) and U.S. Provisional Application Ser. No. 61/263,531, filed on Nov. 23, 2009 (expired), the disclosures of which are incorporated by reference in their entireties.

TECHNICAL FIELD

The present invention relates generally to an extractor device and method for removing tubular body members, such as blood vessels, from the body of a human or animal.

BACKGROUND

Tubular body members generally include blood vessels (such as arteries and veins), tendons, bile ducts and other generally tubular structures found or used within a human or animal body. Such tubular structures are sometimes removed, either for use somewhere else in the body or simply because removal is desired or necessary. For example, the long saphenous vein (LSV), located in subcutaneous fatty tissue in an anteromedial compartment of the lower leg and thigh, is sometimes removed for use in various procedures, such as arterial bypass surgery and preparing an arteriovenus loop for dialysis, etc. The length of the harvested LSV may vary generally from 20 cm to 100 cm.

Phlebology is the medical discipline that involves the diagnosis and treatment of disorders of venous origin. The venous system in the legs consists of a deep venous system and a superficial system. For example, in the deep venous system the femoral veins are important, while in the superficial system the long and short saphenous veins are important veins. The superficial system is also comprised of veins confined to the subcutaneous fatty tissue that can be varicose in nature.

Traditionally, these blood vessels have been removed either by making a long incision along the leg from about the ankle to the groin, or by making a series of multiple, bridged incisions. Tissue (primarily fat) including the blood vessel is dissected from the leg through the incision(s) and the blood vessel is then dissected from the surrounding tissue. These procedures can be time-consuming and/or painful for the patient. Further, the harvested vein must be extensively handled in order to remove the surrounding tissue, which can result in damage to the blood vessels.

It is desirable to provide a device and method for quickly extracting tubular structures while minimizing patient discomfort and handling of the tubular structure. Additionally, it is desirable to provide a device that is strong and durable, so as to capable of use in a variety vein size and thickness, while actuating in a generally longitudinal direction relative to the tubular structure so as to minimize patient discomfort.

SUMMARY

Briefly, an aspect of the invention relates to a device for extracting a tubular structure from tissue, which includes a handle having an actuator, an elongate body with a first end coupled to and extending from the handle, the elongate body having a channel extending through it, an operational head disposed at a second end of the elongate body, the operational head being longitudinally movable between a neutral position and an actuated position and the actuator being operatively coupled to the operational head and configured to actuate longitudinal movement of the operational head relative to the second end of the elongate body.

Another aspect of the invention relates to the operational head being coupled to the actuator and configured for longitudinal movement relative to the second end of the elongate body without movement laterally or radially outward relative to the second end of the elongate body.

Another aspect of the invention relates to the operational head being resiliently biased such that the operational head retracts upon release of the actuator.

Another aspect of the invention relates to the operational head being configured for movement between a retracted position and an extended position.

Another aspect of the invention relates to the actuator being configured as a plunger for extending the operational head upon actuation.

Another aspect of the invention relates to the elongate body being sized for insertion into a tubular structure to be removed.

Another aspect of the invention relates to the operational head including an end cap and hook wire, wherein the end cap and elongate body cooperate to enclose the hook wire when the operational head is in a retracted position.

Another aspect of the invention relates to the operational head including a hook wire having a forwardly-extending member and a rearwardly-extending member coupled by an elbow, wherein the rearwardly-extending member is configured to puncture and/or engage a wall of a tubular structure to be removed.

Another aspect of the invention relates to the device including a light positioned to illuminate the operational head and/or a portion of the elongate member.

Another aspect of the invention relates to exposing and cutting a proximal end of the tubular structure, exposing and cutting a distal end of the tubular structure, inserting the device into the proximal end of the tubular structure until the operational head is proximate the distal end of the tubular structure, actuating the actuator to extend the operational head forward, engaging and securing the distal end of the tubular structure, and removing the device to invaginate the tubular structure.

Another aspect of the invention relates to a device for removing a blood vessel from a tissue, which includes a shaft having a proximal end and a distal end, a handle operatively coupled to the proximal end of the shaft, the handle including an actuator, and an operational head disposed at the distal end of the shaft, the operational head being operatively coupled to the actuator and configured for forward movement relative to the distal end of the shaft upon actuation of the actuator.

Another aspect of the invention relates to the operational head being operatively coupled to the actuator and configured for forward movement relative to the distal end of the shaft without movement laterally or radially outward upon actuation of the actuator.

Another aspect of the invention relates to the operational head being resiliently biased such that the operational head retracts upon release of the actuator.

Another aspect of the invention relates to the operational head including a resilient hook member.

Another aspect of the invention relates to the operational head including a tip disposed over a portion of the resilient hook member.

Another aspect of the invention relates to the operational head including a resilient, non-deformable hook member.

Another aspect of the invention relates to the operational head including a hook member having a distally-extending member and a proximally-extending member coupled by an elbow.

Another aspect of the invention relates to the proximally-extending member including a tip configured to engage a vein when the operational head is in an extended position.

Another aspect of the invention relates to the hook member being disposed within the distal end of the shaft when the operational head is in a retracted position.

Another aspect of the invention relates to the operational head including a single hook member.

Another aspect of the invention relates to the shaft being sized for insertion into a blood vessel to be removed.

Another aspect of the invention relates to the shaft being configured to include a bend of about 10 degrees adjacent the proximal end.

Another aspect of the invention relates to the shaft being configured to include a bend of about 10 degrees to about 20 degrees adjacent the proximal end.

Another aspect of the invention relates to the shaft being approximately circular in cross section and the distal end of the shaft being approximately oblong is cross section.

Another aspect of the invention relates to the operational head being retractable.

Another aspect of the invention relates to the handle including a gripping member and the actuation member being configured as a plunger.

Another aspect of the invention relates to the gripping member including a pair of outwardly extending members configured for engagement by a user's index finger and middle finger and the actuation member being configured for actuation by the user's thumb.

Another aspect of the invention relates to the handle and actuation member being configured to be actuated like a syringe.

Another aspect of the invention relates to exposing and cutting a proximal end of the blood vessel, exposing and cutting a distal end of the blood vessel, inserting an extraction device into the proximal end of the blood vessel, the extraction device having a shaft having a proximal end and a distal end, a handle operatively coupled to the proximal end of the shaft, the handle including an actuator, and an operational head disposed at the distal end of the shaft, the operational head including a hook member operatively coupled to the actuator and configured for forward movement relative to the distal end of the shaft upon actuation of the actuator, positioning the extraction device such that the operational head is proximate the distal end of the blood vessel, actuating the actuator to extend the operational head forward without extending the operational head laterally or radially outward, engaging and securing the distal end of the blood vessel, and removing the extraction device to remove the blood vessel.

Another aspect of the invention relates to engaging and securing the distal end of the blood vessel including releasing the actuator, thereby retracting the operational head of the extraction device.

Additional aspects are related to methods of extracting tubular structures from the body, as will be understood from the disclosure herein.

Even further aspects of the devices and methods of this invention will become readily apparent upon review of the detailed description of illustrative embodiments, taken in conjunction with the accompanying drawings.

BRIEF DESCRIPTION OF THE FIGURES

Exemplary embodiments of the invention will now be described in conjunction with the following drawings, in which.

DESCRIPTION OF THE ILLUSTRATIVE EMBODIMENTS

Figure 1:
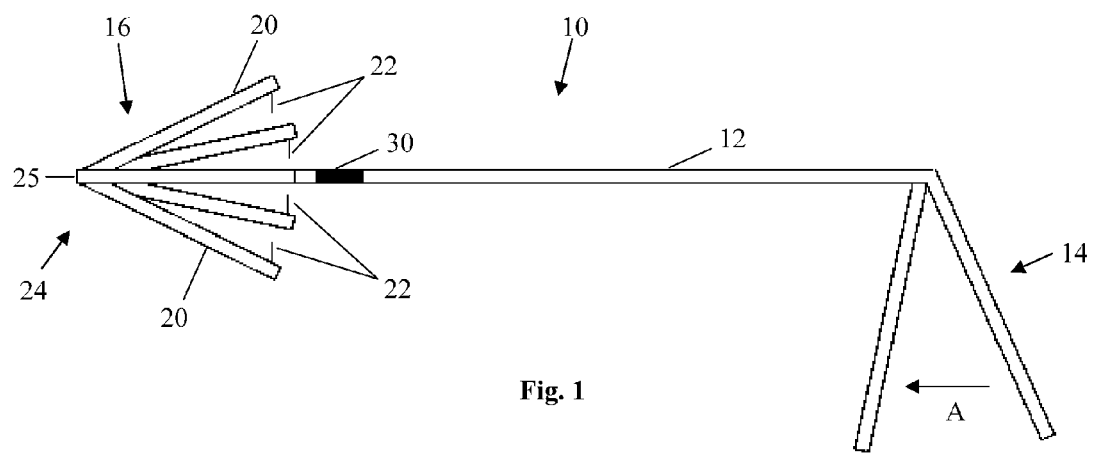
FIG. 1 is a side view of an embodiment of an example extractor for tubular structures illustrated in an expanded position.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

A blood vessel extraction device may be configured to include multiple engagement members that extend laterally and/or radially outward from the device body (relative to the length of the blood vessel) upon actuation. The multiple engagement members may be configured to cut and/or engage a portion of the blood vessel so that the blood vessel may be extracted upon removal of the extraction device. This configuration requires that the multiple engagement members be flexible enough for lateral or radial outward extension. This lateral or radial outward flexibility may result in vessel engagement members that are insufficiently rigid to maintain structural integrity when subjected to forces sufficient to extract a blood vessel from tissue.

Aspects of the present disclosure recognize shortcomings with designs that include multiple engagement members that extend laterally or radially outward from the device body (relative to the length of the blood vessel), and provide a device for extracting blood vessels that includes an operational head with an engagement member of sufficient strength and rigidity to withstand the forces necessary for removal of blood vessels. The blood vessel extraction device includes a shaft having a proximal end and a distal end, a handle operatively coupled to the proximal end of the shaft, where the handle includes an actuator. An operational head is disposed at the distal end of the shaft, with the operational head being operatively coupled to the actuator and configured for forward movement relative to the distal end of the shaft without movement laterally or radially outward upon actuation of the actuator. In a preferred embodiment, the operational head comprises a single hook member that, when actuated, extends longitudinally forward without extending laterally or radially outward An extractor is disclosed and adapted to facilitate the removal of tubular body members from the body of a human or animal. As used herein, tubular body members is intended to include blood vessels, such as arteries and veins, tendons, bile ducts and other generally tubular structures found or used within a human or animal body, either natural or artificial. In one example, the extractor can be used to facilitate removal of varicose veins. Moreover, the extractor is intended to be used to extract, retract, harvest, dissect, displace and/or remove one or more tubular body member(s) from the body. However, in other examples, the extractor can be used to insert and/or place one or more tubular body member(s) into the body.

The extractor is intended to be a surgical instrument, and can be formed of materials and made using manufacturing techniques suitable to meet surgical operation and cleanliness standards. For example, the extractor can be formed from a relatively soft material, such as plastic, suitable for passing through the selected tubular body member without damage to the internal surface of the tubular body member. In addition or alternatively, various other rigid or non-rigid materials can be used, such as various metals, hard rubbers, etc. In addition or alternatively, a portion or all of the extractor 10 can have some flexibility. The extractor can be designed for single use (e.g., disposable) or multiple uses (e.g., non-disposable and able to be sterilized).

Figure 2:
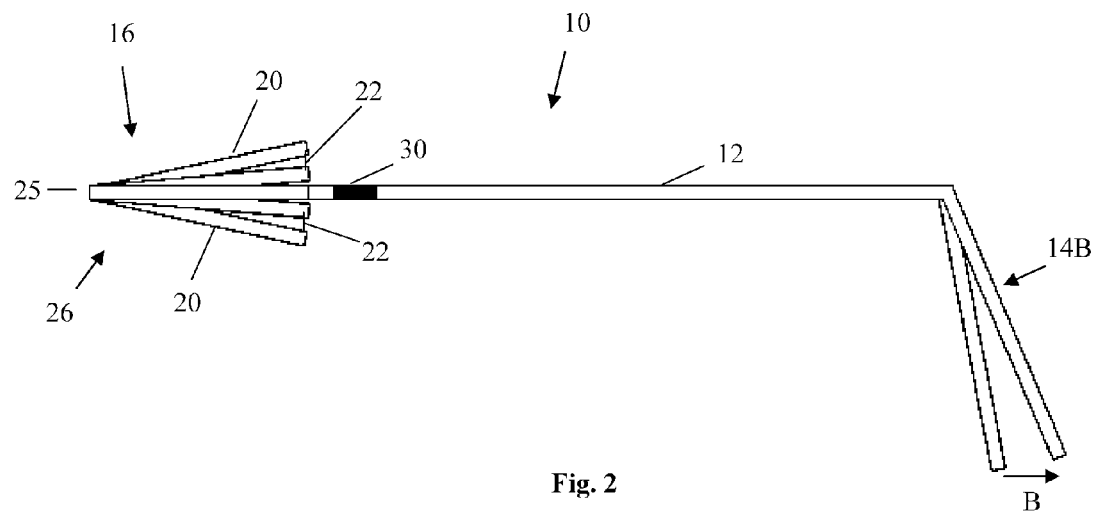
FIG. 2 is similar to FIG. 1, but illustrated in the retracted position.

Turning more specifically to one embodiment shown in FIGS. 1 and 2, an example extractor 10 for tubular body members is illustrated. The extractor 10 generally includes an elongate body 12 (or shaft) with a handle 14 disposed at one end and an operational head 16 disposed at the other end. Generally, the elongate body 12 and the operational head 16 have a cylindrical geometry and have a diameter (or width) generally equal to or less than the inner diameter of the tubular body member (e.g., blood vessel) that the extractor 10 will be inserted into. The handle 14 can have various structures, grips, etc. to facilitate manipulation of the extractor 10 by a user (e.g., a doctor), and is generally intended to remain outside the patient's body.

The operational head 16 of the extractor 10 can have various geometries, such as an expanding bullet shape. In one example, as shown in FIG. 1, the expanding bullet shape can have an expandable umbrella shape formed from a plurality of rigid or non-rigid expandable elements 20. For example, the extendable elements 20 can radially expand via an umbrella-style mechanism. In one example, a central control post (not shown) can extend within the length of the elongate body 12 between the handle 14 and the operational head 16. One or more connecting ribs (not shown) can be pivotally coupled to the control post and to one or more extendable elements 20, such that movement of the control post (i.e., via the handle 14) can drive the connecting rib(s) to thereby drive the extendable elements 20 to expand or contract the head 16 similar to the opening of an umbrella. Various other mechanisms can also be used to enable extension of the extendable elements 20 in an umbrella-like manner.

Additionally, the expandable elements 20 can be disposed about the distal end of the extractor 10, such as at the distal end of the elongate body 12. The expandable elements 20 can be disposed at the distal end 25, or near the distal end 25. For example, where the expandable elements 20 are pivotally coupled to the distal end 25 of the extractor 10, they will expand the head 16 outwardly and rearward from the distal end 25 of the extractor 10. Thus, when the distal end 25 is positioned beyond the end of the vein to be removed, the outwardly-expanded head 16 will grasp the end portion of the previously cut vein wall. Upon pulling the extractor 10 backwards, the outwardly-expanded head 16 will cause the vein to be inverted upon itself as the instrument is moved out of the body to thereby remove the vein. Thus, because the expandable elements 20 generally do not extend forwardly from the distal end 25 but instead extend rearwardly, operation of the extractor 10 utilizes a previously cut vein wall for grasping to thereby remove the vein from the body.

Various numbers and/or geometries of expandable elements 20 can be utilized. In addition, any or all of the expandable elements 20 can include gripping structure, such as one or more gripping projections 22 extending outwardly therefrom, for grasping a portion of the tubular structure, such as a vein wall or the like. It is to be understood that various other structures can be provided to enable the expanding elements 20 to radially expand and retract to a desired distance, including manually-operated and/or power-operated (electrical, pneumatic, hydraulic, etc.) structure. Additionally, webbing (not shown) or the like can be provided between some or all of the expandable elements 20.

The operational head 16 can be selectively movable between an expanded position 24, as illustrated in FIG. 1, and a retracted position 26, as illustrated in FIG. 2. The handle 14 can be used to actuate the operational head 16 for operation between the expanded 24 and retracted 26 positions. For example, as shown in FIG. 1 a portion of the handle 14 can be moved in the direction of arrow A to move the operational head 16 to the expanded position 24. Alternatively, as shown in FIG. 2 a portion of the handle 14B can be moved in the direction of arrow B to move the operational head 16 to the retracted position 26. It is to be understood that the movement of the handle 14 is shown schematically, and that movement towards the shown directions A and B is arbitrary. It is to be further understood that the operational head 16 can also be moved to an intermediate position between the expanded 24 and retracted 26 positions via operation of the handle 14 to an intermediate position between those illustrated herein.

In addition or alternatively, the head 16 can be resiliently biased towards either of the expanded 24 or retracted 26 positions. The head 16 can be resiliently biased in various manners, such as by a spring or the like. In the shown example, the head 16 is biased towards the expanded position 24, such that a user is required to move the handle 14B towards the direction of arrow B to collapse the head 16 towards the retracted position 26 of FIG. 2. Upon release of the handle 14B, the head 16 can be resiliently biased back towards the expanded position 24. Still, it is to be understood that the head 16 can be biased towards either of the expanded 24 or retracted 26 positions, and that operation of the handle towards either of the directions A or B can be suitably modified to provide a desired operational mechanism. Furthermore, although one example illustration of the handle 14 is provided herein, it is to be understood that the handle can have various structure, geometry, operation, etc. For example, the handle can remain generally stationary, while an additional trigger or the like (not shown) is utilized to selectively actuate movement of the head 16.

As described above, the handle 14 remains on the exterior of the patient's body and is used to guide the movement of the extractor 10. More specifically, the handle 14 can be used to guide movement of the head 16 through the tubular body, and then to selectively actuate expansion or retraction of the head 16 at a desired time. Additionally, the handle 14 can also be used to operate various other features of the extractor 10. In one example, the extractor 10 can include a light 30 for providing illumination within the tubular member. The light 30 can provide illumination that is visible from outside of the patient's body to provide a reference to help the user guide the head 16 along the interior of the tubular member. The light 30 can be provided by various structures, such as light bulbs, LEDs, fiber optics, lasers, etc., and can be powered by electrical or chemical structure. The light 30 can emit various types of light (e.g., visible light, ultraviolet light, infrared light, etc.) in various colors and/or operational modes (steady, pulsing, etc.). It is to be understood that the light 30 can be provided at various locations on the extractor 10 (e.g., at the distal end 25, along the length of the central tube 12, etc.), and can include one or more sources of light. In addition or alternatively, a suitable power source and/or operation switch (not shown) can be provided within the extractor 10 and/or coupled to the extractor 10 by cables, etc.

By way of example, in operation, a proximal incision can be made through the vein at a proximal end, and a distal incision can be made through the vein at a distal end. The length of the vein between the proximal and distal ends generally defines the length of vein to be removed at this stage. The operational head 16 of the extractor 10 is maintained in the retracted position 26 (e.g., by moving the handle 14B in the direction of arrow B in FIG. 2). The operational head 16 is inserted into the vein through the proximal end and is moved through the vein until the head 16 moves beyond the distal end of the vein. The light 30, if present, can guide the user along the length of the vein, which can have a tortuous path. Once the end 25 of the extractor 10 is located beyond the distal end of the vein, the handle 14 is operated (e.g., by moving the handle 14 in the direction of arrow A in FIG. 1) to move the head 16 outwardly to the expanded position 24.

The expanded operational head 16 is able to grasp a portion of the vein walls about the distal end of the vein, via the expandable elements 20 capturing the distal end of the vein. For example, the operational head 16 can expand to a relatively greater diameter than the outer diameter of the vein so as to completely capture the distal end of the vein. The extractor 10 is then pulled backwards out of the body. The distal end of the vein, being captured by the expanded head 16, is caused to invert upon itself as the extractor 10 is moved out of the body. Meanwhile, the head 16 continues to grasp the outer walls of the vein to separate it away from its surrounding connecting tissue. The entire vein (e.g., defined between the proximal and distal ends of the vein) can then be pulled out of the proximal incision. If the vein is too long for removal by the extractor 10 via a single usage, a third incision can be made through the vein at a third location. The extractor 10 can be inserted through the distal incision and moved through the vein to the third incision, repeating the above process until the desired amount of vein is removed. In this way, it is estimated that the time required for removal of a vein may be reduced from approximately 1.5 hours down to about 0.5 hours.

Turning to FIGS. 3-8, another exemplary embodiment of an extractor 10 for tubular body members is illustrated. The extractor 10 is illustrated schematically as being located within an example tubular body member 15, such as a vein. The extractor 10 generally includes an elongate body 12 with a handle 14 disposed at one end and an operational head 16 disposed at the other end. Generally, the elongate body 12 has a cylindrical geometry and has a diameter (or width) generally equal to or less than the inner diameter of the tubular body member 15 that the extractor 10 will be inserted into, though it can also have various sizes to accommodate different size veins, etc. Additionally, the extractor 10 can have various overall lengths to accommodate different lengths of veins to be removed and/or size of patients, etc. Optionally, the elongate body 12 can be a tube-in-tube design (not shown). For example, the elongate body 12 can be catheterized, placed in a cannula, etc. The handle 14 can have various structures, grips, etc. to facilitate manipulation of the extractor 10 by a user (e.g., a doctor), and is generally intended to remain outside of the patient's body. The handle 14 can be separate from, or even coupled to, the elongate body 12 (or even a catheter, cannula, etc., if any). For example, the handle 14 can be coupled to, such as formed with, the elongate body 12, and can be de-coupled therefrom only when it is desired to operate the handle 14. In one example, the handle 14 can be formed with or coupled to (e.g., via an adhesive, welding, etc.) the elongate body 12, and can be de-coupled therefrom by "breaking off" the handle 14 when it is desired to operate the handle 14.

Figure 3:
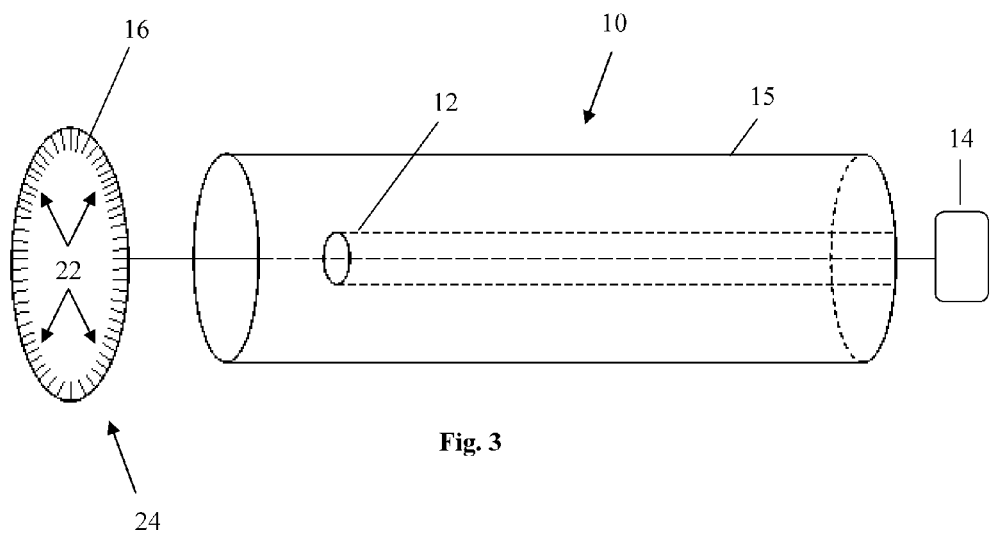
FIG. 3 is a side view of another embodiment of an example extractor for tubular structures.

The operational head 16 of the extractor 10 can have various geometries, such as an expandable and collapsible loop or snare. In one example, as shown in FIG. 3, the operational head 16 can be formed from at least one generally flexible wire or suture. In another example, the operational head 16 can be formed of a plurality of wires or sutures, that can be braided or woven together to form a unitary wire or suture, or can even remain independent as a plurality of independently operable wires or sutures. In addition or alternatively, the flexible wire or suture can be dissolvable or non-dissolvable by various liquids, the patient's body, etc. The operational head 16 can radially expand and collapse to a relatively greater or lesser diameter. In one example, a central control post (not shown) can extend within the length of the elongate body 12 between the handle 14 and the head 16 such that movement of the control post (i.e., via the handle 14) can cause the head 16 to expand or collapse to adjust the diameter thereof. In another example, a portion of the handle 14 can be directly coupled to the head 16 for adjusting the diameter thereof. For example, the operational head 16 can be configured as a ligature loop with a knot that protrudes from the distal end 25 of the elongate body 12. The opposite end of the suture can be coupled to the handle 14 (or intermediate structure) such that movement of the handle 14 affects opening or closing of the ligature loop (e.g., between an expanded position 24 and a collapsed position 26). During operation, the knot can be held in place by the operator, and/or the knot can have a diameter greater than the distal end 25 of the elongate body 12 such that pulling on the handle 14 does not cause the knot to be drawn into the elongate body 12. Various other mechanisms can also be used to cause the head 16 to expand or collapse.

Additionally, the operational head 16 can be disposed about the distal end of the extractor 10, such as at the distal end of the elongate body 12. The operational head 16 can be disposed at the distal end 25, or near the distal end 25. For example, where the operational head 16 is disposed about the distal end 25 of the extractor 10, it can expand outwardly from the distal end 25 of the extractor 10. Similarly, the operational head 16 can collapse inwardly towards the distal end 25. Thus, when the distal end 25 is positioned beyond the end of the vein to be removed, the outwardly expanded head 16A (see FIG. 5) can grasp the end portion of the previously cut vein wall. Upon pulling the extractor 10 backwards, the collapsed head 16B can cause the vein to be inverted upon itself as the instrument is moved out of the body to thereby remove the vein (see FIGS. 6-7).

Various numbers and/or geometries of operational head 16 can be utilized. For example, the operational head 16 can have a generally circular geometry, though it can also have an elliptical geometry, other curved geometry, polygonal geometry, etc. In addition, the operational head 16 can include gripping structure, such as one or more gripping projections 22 extending inwardly therefrom, for grasping a portion of the tubular body member 15, such as an outer portion of a vein wall or the like. The gripping projections 22 can be rigid or flexible, and can have a sharp edge or be blunt. The gripping projections 22 can be formed with or coupled to the head 16. Generally, the gripping projections 22 can inhibit, such as prevent, slippage between the collapsed head 16B and the tubular body member 15 when the tubular body member 15 is being removed from the patient.

It is to be understood that various other structures can be provided to enable the operational head 16 to radially expand and collapse as desired, including manually-operated and/or power-operated (electrical, pneumatic, hydraulic, etc.) structure. Additionally, where the operational head 16 is formed of a plurality of wires, connecting structure can be provided between the wires. In addition or alternatively, structure can be provided to guide and/or provide support to the head 16 when it is in the expanded position and/or located a distance from the distal end 25 of the elongate body 12.

Figure 4:
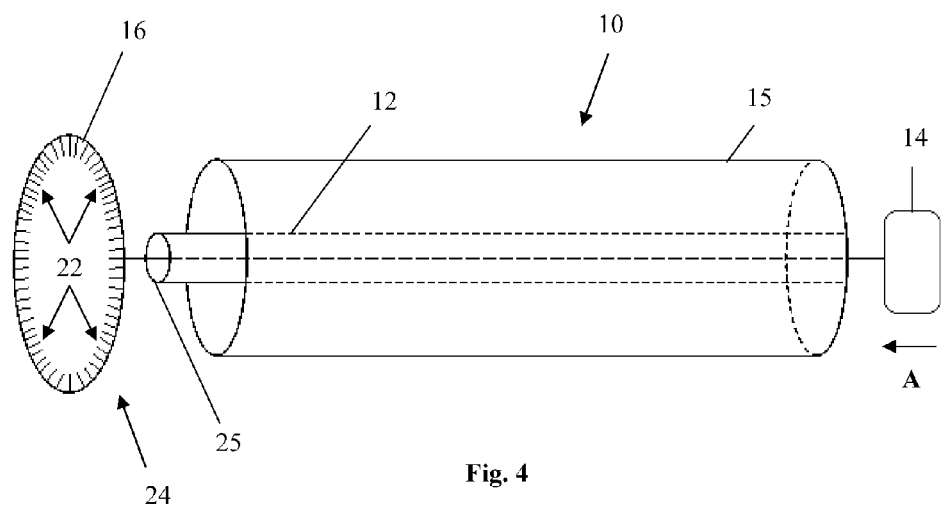
FIG. 4 is similar to FIG. 3, but illustrates the extractor in another position.
Figure 5:
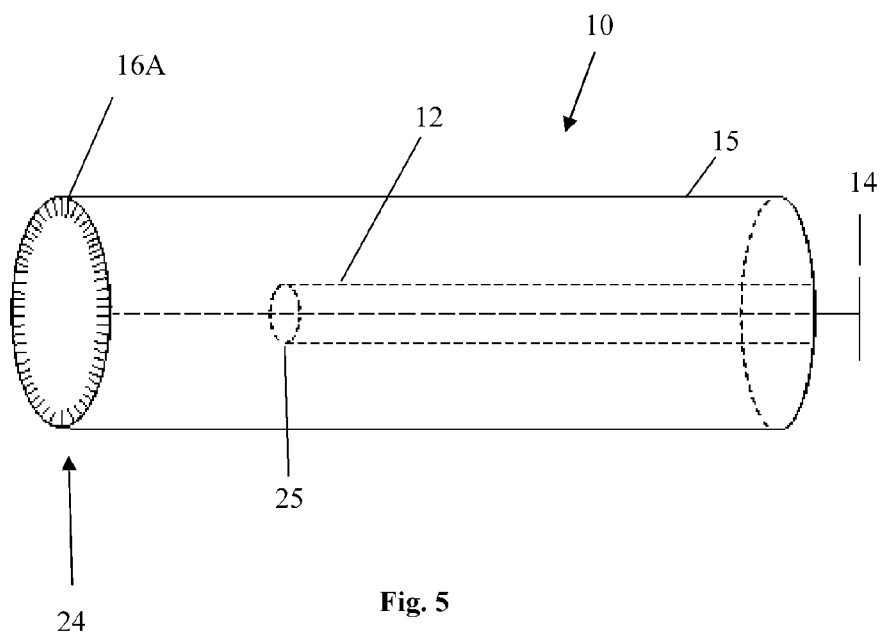
FIG. 5 is similar to FIG. 3, but illustrates the extractor in another position.
Figure 6:
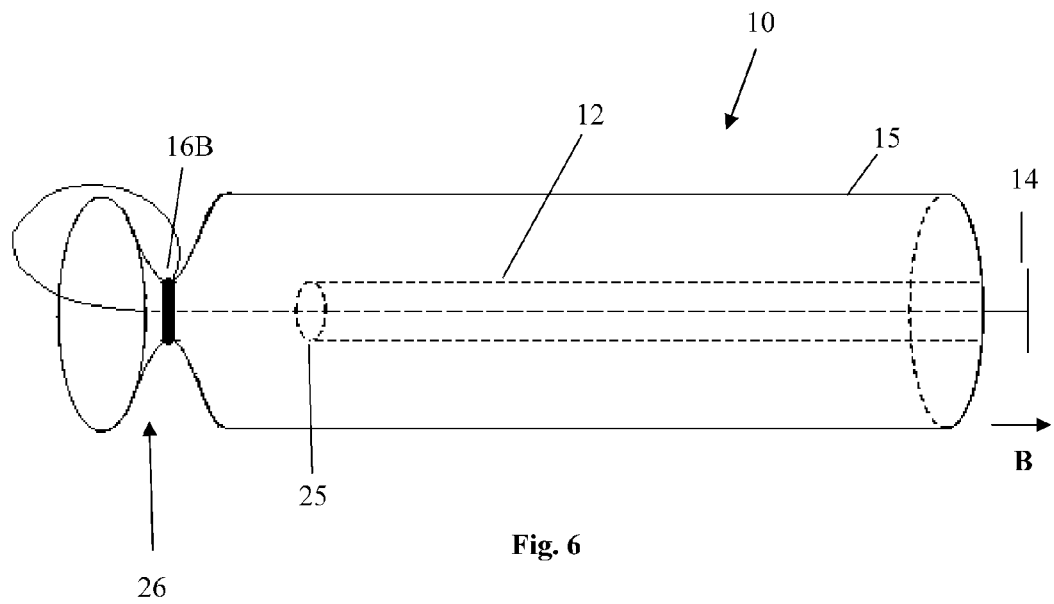
FIG. 6 is similar to FIG. 3, but illustrates the extractor in a clamped position about a portion of the tubular body member.

The operational head 16 can be selectively movable between an expanded position 24 (i.e., FIG. 4) and a collapsed position 26 (i.e., FIG. 6). In one example, the handle 14 can be used to actuate the head 16 for operation between the expanded 24 and collapsed 26 positions. For example, as shown in FIG. 4, a portion of the handle 14 can be moved in the direction of arrow A to move the head 16 to the expanded position 24. Alternatively, as shown in FIG. 6, a portion of the handle 14 can be moved in the direction of arrow B to move the head 16 to the collapsed position 26. It is to be understood that the movement of the handle 14 is shown schematically, and that movement in the shown directions A and B is arbitrary and can be modified. It is to be further understood that the head 16 can also be moved to an intermediate position between the expanded 24 and collapsed 26 positions via operation of the handle 14 to an intermediate position between those illustrated herein.

In addition or alternatively, the head 16 can be resiliently biased towards either of the expanded 24 or collapsed 26 positions. The head 16 can be resiliently biased in various manners, such as by a spring or the like. For example, the head 16 can be biased towards the collapsed position 26, such that a user is required to move the handle 14 towards the direction of arrow A to expand the head 16 towards the expanded position 24 of FIG. 4. Upon release of the handle 14, the operational head 16 can be resiliently biased back towards the collapsed position 26. Still, it is to be understood that the operational head 16 can be biased towards either of the expanded 24 or collapsed 26 positions, and that operation of the handle towards either of the directions A or B can be suitably modified to provide a desired operational mechanism. In addition or alternatively, the operational head 16 can be biased only partially towards the collapsed position 26, such that the operator manipulates the handle 14 to fully clamp the operational head 16 down upon the end of the tubular body member 15. In addition or alternatively, the handle 14 can have a locking feature (not shown) to maintain a position of the operational head 16 in opposition to the spring until released by the operator. Furthermore, although one example illustration of the handle 14 is provided herein, it is to be understood that the handle can have various structure, geometry, operation, etc.

For example, the handle can remain generally stationary, while an additional actuator, such as a trigger or the like (not shown), is utilized to selectively actuate movement of the head 1.

As described above, the handle 14 remains on the exterior of the patient's body and is used to guide the movement of the extractor 10. More specifically, the handle 14 can be used to guide movement of the head 16 through the tubular body, and then to selectively actuate expansion or retraction of the head 16 at a desired time. Additionally, the handle 14 can also be used to operate various other features of the extractor 10, for example, the light 30 disclosed in earlier and illustrated in FIGS. 1 and 2 can similarly be disposed on the extractor 10 discussed in FIGS. 3-8.

Figure 8:
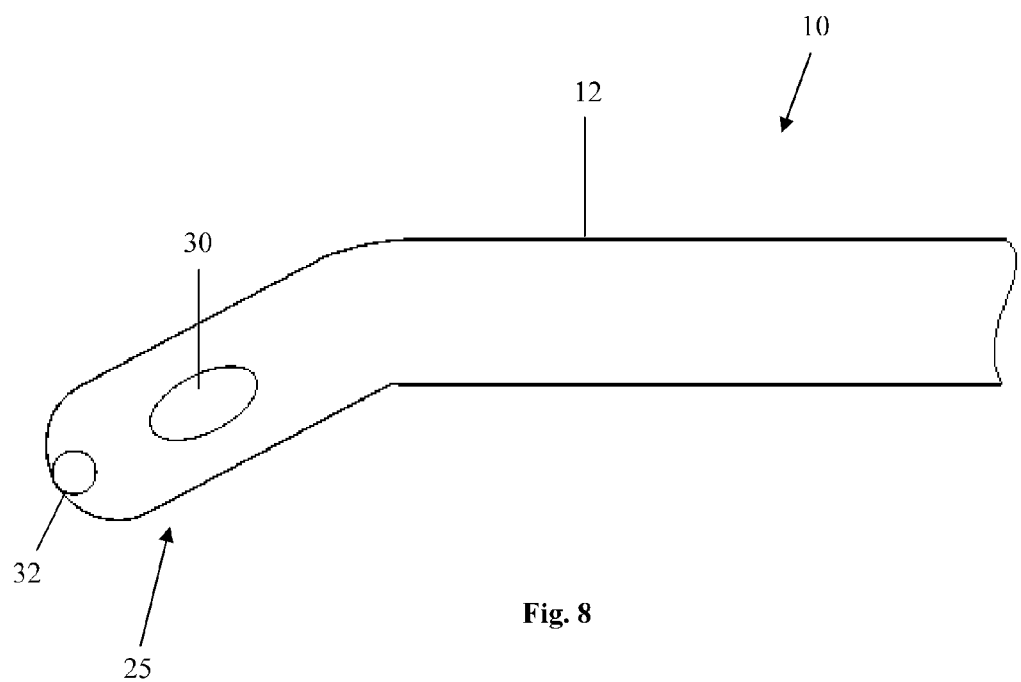
FIG. 8 is a detail view of an example end of the extractor of FIG. 3.

Keeping with FIG. 8, the central tube 12 can be generally rigid, or can have at least a portion that is flexible. For example, all of the central tube 12 can be flexible. In another example, only a predetermined portion can be flexible, such as the distal end 25. The central tube 12 can be adapted to maintain a desired flexible position, or can be continuously flexible so as to constantly adjust to the tortuous path of a vein. In addition or alternatively, the distal end 25 can have a generally curved and/or tapered end. In addition or alternatively, the distal end 25 can have an opening 32 for extending the operational head 16 therefrom. In addition or alternatively, the distal end 25 and/or the operational head 16 can have a cooperating stop structure (not shown) to inhibit accidentally pulling the head 16 into the central tube 12. Still, in other examples, some or all of the head 16 may be retractable within the central tube 12.

In operation, the device illustrated in FIGS. 3-8 has similarities to the extractor of FIGS. 1 and 2. A proximal incision can be made through the vein at a proximal end, and a distal incision can be made through the vein at a distal end. The length of the vein between the proximal and distal ends generally defines the length of vein to be removed at this stage. The operational head 16 of the extractor 10 is initially maintained in the collapsed position 26 (e.g., by moving the handle 14 in the direction of arrow B and/or by a resilient biasing action). The distal end 25 of the central tube 12 is inserted into the vein through the proximal end and is moved through the vein until the distal end 25 moves beyond the distal end of the vein. The light 30, if present, can guide the user along the length of the vein, which can have a tortuous path. Once the distal end 25 of the extractor 10 is located beyond the distal end of the vein, the handle 14 is operated (e.g., by moving the handle 14 in the direction of arrow A in FIG. 4 and/or by a resilient biasing action) to expand the head operational 16 outwardly to the expanded position 24. In addition or alternatively, a portion of the end of the vein can be withdrawn from the patient's body, via the distal incision, to facilitate clamping the head 16 thereabout.

The expanded head 16A is able to grasp a portion of the vein walls about the distal end of the vein, via the gripping projections 22, to capture the distal end of the vein. For example, the head 16 can expand to a generally equal to or greater diameter (see FIG. 5) than the outer diameter of the vein. The head 16 of the extractor 10 is then moved to the reduced diameter, collapsed position 26 (e.g., by moving the handle 14 in the direction of arrow B as shown in FIG. 6) so as to clamp down on and completely capture the distal end of the vein.

Figure 7:
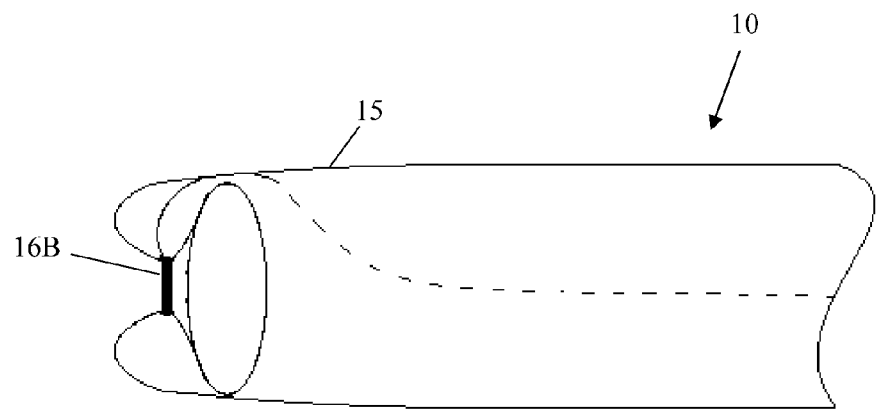
FIG. 7 is a side view of an example method of removing the tubular body member.

The extractor 10 is then pulled backwards out of the body along the direction of arrow C (see FIG. 7). The distal end of the vein, being captured by the expanded head 16A, is caused to invert upon itself as the extractor 10 is moved out of the body. Meanwhile, the head 16 continues to grasp the outer walls of the vein to separate it away from its surrounding connecting tissue. The entire vein (e.g., defined between the proximal and distal ends of the vein) can then be pulled out of the proximal incision. If the vein is too long for removal by the extractor 10 via a single usage, a third incision can be made through the vein at a third location. The extractor 10 can be inserted through the distal incision and moved through the vein to the third incision, repeating the above process until the desired amount of vein is removed. Again, it is estimated that removal of a vein may occur in approximately 0.5 hours instead of 1.5 hours.

Another embodiment of an extractor 10 for removing tubular body members is illustrated in FIGS. 9-12. The extractor 10 generally includes an elongate body 12 (also referred to as a shaft) with a handle 14 disposed at one end and an operational head 16 disposed at the other end. In accordance with one embodiment, the elongate body or shaft 12 and the operational head 16 have a cylindrical geometry and have a diameter (or width) generally equal to or less than the inner diameter of the tubular body member (e.g. blood vessel) that the extractor 10 will be inserted into. In accordance with another embodiment, the majority of the shaft is substantially circular in cross section, while the distal portion of the shaft (adjacent the operational head 16) is substantially oblong in cross section.

In accordance with one embodiment, the elongate body or shaft 12 is configured to be angled between approximately 10 and 20 degrees adjacent its proximal end. In accordance with another embodiment, the elongate body or shaft 12 is angled approximately 10 degrees adjacent the proximal end. The angling of the shaft is selected to facilitate smooth and controllable insertion of the device into a blood vessel. Although the handle 14 can have various structures, grips, etc. (e.g., a plunger) to facilitate manipulation of the extractor 10 by a user (e.g., a doctor), it is illustrated here as a syringe with an actuator or button 18 for actuating the handle 14. The exemplary syringe-style handle is illustrated as having two symmetrical outwardly extending members 14A and 14B configured to be engaged, for example, by the user's index finger and middle finger. The actuator or button 18 is longitudinally movable between a neutral position (also referred to as a retracted position) and an actuated position (also referred to as an extended position) relative to the elongate body 12. The handle 14 is generally intended to remain outside the patient's body. Additionally, as discussed in previous embodiments, a light 30 may be disposed on the handle for providing illumination within the tubular member.

The operational head 16 can have various geometries, although here it is illustrated as having an end cap 17 and a resilient hook wire 23, wherein the end cap 17 and the elongate body 12 cooperate to enclose the hook wire 23 when the operational head 16 is in a retracted position. The end cap 17 comprises an atraumatic tip configured to guide the elongated body 12 through a tubular structure while avoiding unwanted perforation of the tubular structure. In the illustrated embodiment, the hook wire 23 comprises a forwardly-extending member 23A and a rearwardly-extending member 23B coupled by an elbow 23C. The rearwardly-extending member 23B is configured to puncture and/or engage a wall of a tubular structure to be removed. The resilient hook wire 23 may be deformable or non-deformable. In a preferred embodiment, the resilient hook wire 23 is constructed to be rigid and non-deformable under forces normally encountered during blood vessel extraction. It will be appreciated that, although the figures illustrate a single hook wire, the device may be configured with more than one hook wire capable of longitudinal extension with respect to the elongate body.

Figure 9:
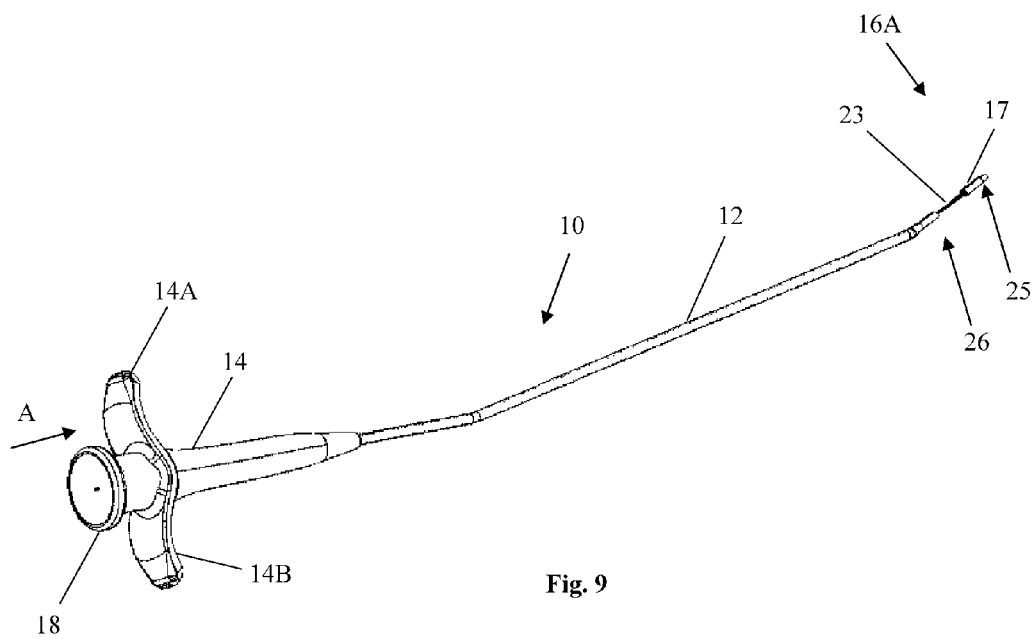
FIG. 9 is a perspective view of another embodiment of an extractor.
Figure 10:
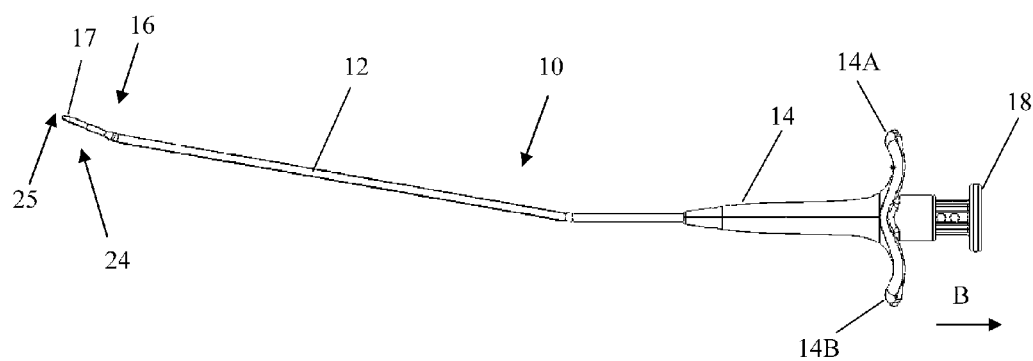
FIG. 10 is similar to FIG. 9, but illustrates a side view of the extractor.
Figure 11:
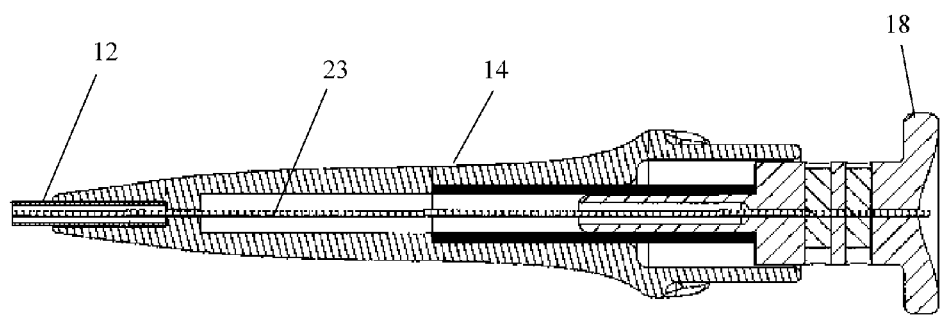
FIG. 11 is similar to FIG. 9, but illustrates a cross-section view of the handle of the extractor.
Figure 12:
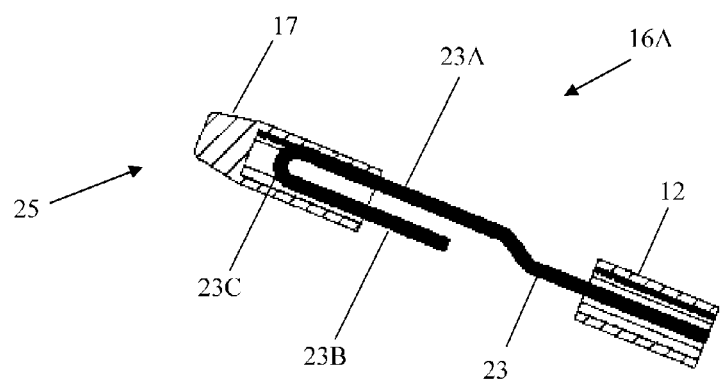
FIG. 12 is similar to FIG. 9, but illustrates a cross-section view of the operational head in an actuated position.

The operational head 16 can be selectively movable between an actuated position 26 (shown in FIG. 9) and a neutral position 24 (shown in FIG. 10). The button 18 on the handle 14 actuates the operational head 16 for transitioning between the actuated 26 and neutral 24 positions. For example, as shown in FIG. 9, depressing the button 18 so that it moves in the direction of the arrow A actuates the operational head 16, such direction being longitudinally with respect to the distal end of the elongate body 12 as opposed to lateral or radial movement. As shown in FIG. 10, releasing the button 18 so that it moves in the direction of arrow B allows the operational head 16 to return to a neutral position. The operational head 16 can also be moved to an intermediate position between the actuated 26 and neutral 24 positions via operation of the handle 14 to an intermediate position. Movement of the handle 14 is shown schematically, with the movement towards the shown directions of A and B being arbitrary.

In addition or alternatively, the operational head 16 can be resiliently biased towards either of the expanded 26 or retracted 24 positions. The operational head 16 can be resiliently biased in various manners, such as by a spring or the like. In the shown example, the operational head 16 is biased towards the retracted position 24 (shown in FIG. 10), such that a user is required to move the handle 14A towards the direction of arrow A to actuate the operational head 16 towards the expanded position 26 of FIG. 9. Upon release of the handle 14A, the head 16 can be resiliently biased back towards the retracted position 24 of FIG. 10. Still, it is to be understood that the head 16 can be biased towards either of the expanded 26 or retracted 24 positions, and that operation of the handle towards either of the directions A or B can be suitably modified to provide a desired operational mechanism. Furthermore, although one example illustration of the handle 14 is provided herein, it is to be understood that the handle can have various structure, geometry, operation, etc. For example, the handle can remain generally stationary, while an additional trigger or the like (not shown) is utilized to selectively actuate movement of the head 16.

In operation, the device illustrated in FIGS. 9-12 has similarities to the previous embodiments. An incision can be made through the vein at a proximal end as well as at a distal end. The head 16 of the extractor 10 is initially maintained in the neutral position 26. Beginning with the end cap 17 the extractor 10 is inserted into the vein through the proximal incision and is moved through the vein until the operational head 16 is positioned proximal to the distal end of the vein (e.g., beyond the distal end of the vein). The light 30, if present, can guide the user along the length of the vein, which can have a tortuous path. Once the distal end 25 of the extractor 10 is located proximal the distal end of the vein (e.g., beyond the distal end of the vein), the actuator 18 of the handle 14 is operated (e.g., by moving the handle 14 in the direction of arrow A in FIG. 9 and/or by a resilient biasing action) to expand the head 16 longitudinally to the expanded position 26. It should be noted that actuation protrudes the head longitudinally relative to the distal end of the elongate body 12 without movement laterally or radially outward relative to the shaft and/or the vein. In addition or alternatively, a portion of the end of the vein can be withdrawn from the patient's body, via the distal incision, to facilitate clamping or otherwise engaging the operational head 16 thereabout.

The actuated head 16A is positioned such that the edge of the vein is generally located between the forwardly-extending member 23A and the rearwardly-extending member 23B.

The actuator 18 is slowly released and the operational head 16 engages or otherwise captures the distal end of the vein as the operational head 16 transitions to its neutral position 26. Meanwhile, the rearwardly-extending member 23B grasps and/or punctures the vein.

The extractor 10 is then pulled backwards out of the body. The distal end of the vein, being captured by the operational head 16, is caused to invert upon itself as the extractor 10 is moved out of the body. Meanwhile, the head 16 continues to grasp the outer walls of the vein to separate it away from its surrounding connecting tissue. The entire vein (e.g., defined between the proximal and distal ends of the vein) can then be pulled out of the proximal incision. If the vein is too long for removal by the extractor 10 via a single usage, a third incision can be made through the vein at a third location. The extractor 10 can be inserted through the distal incision and moved through the vein to the third incision, repeating the above process until the desired amount of vein is removed. Again, it is estimated that removal of a vein may occur in approximately 0.5 hours instead of 1.5 hours.

In addition or alternatively, the extractor 10 can include various other additional features. Various examples (none shown) can include any or all of: cutting elements; cameras, cauterizing elements; suction elements, liquid or gas sprays; other laparoscopic equipment; etc.

The invention has been described with reference to the example embodiments described above. Modifications and alterations will occur to others upon a reading and understanding of this specification. Examples embodiments incorporating one or more aspects of the invention are intended to include all such modifications and alterations. It is to be understood that various other more or less steps in using the device can be performed, any of which can be performed in various orders.

What is claimed is:

1. A method for extracting a tubular structure from tissue using a device including a handle having an actuator, an elongate body with a first end coupled to and extending from the handle, and an operational head coupled with the elongate body and disposed at a second end thereof, wherein the operational head further comprises a radially expandable and collapsible snare, configured to grasp the tubular structure when the snare is collapsed, the method comprising:
   inserting the elongate body into the tubular structure with the snare in a collapsed position;
   placing the snare into an expanded position by operating the actuator;
   surrounding the tubular structure with the expanded snare by operating the actuator;
   grasping a portion of the tubular structure with the snare by operating the actuator to collapse the snare on the tubular structure; and
   pulling the tubular structure from the tissue by moving the snare relative to the tissue and inverting the tubular structure upon itself with the collapsed snare and extracting the tubular structure from the tissue.

2. The method of claim 1, wherein the snare is resiliently biased such that the snare moves to the collapsed position upon release of the actuator.

3. The method of claim 1, wherein the actuator is configured as a trigger, and placing the snare into the expanded position further comprises:
   actuating the snare with the trigger.

4. The method of claim 1, further comprising:
   using a light positioned at the second end to illuminate the snare and/or a portion of the elongate body.

* * * * *